United States Patent [19]

Webb et al.

[11] Patent Number: 5,699,806

[45] Date of Patent: Dec. 23, 1997

[54] ULTRASOUND SYSTEM WITH NONUNIFORM ROTATION CORRECTOR

[75] Inventors: Peter Webb, Menlo Park; Edward Verdonk, San Jose, both of Calif.

[73] Assignee: Hewlett-Packard Company, Palo Alto, Calif.

[21] Appl. No.: 724,203

[22] Filed: Oct. 1, 1996

[51] Int. Cl.[6] ........................................... A61B 8/12
[52] U.S. Cl. ........................... 128/667.06; 128/660.09
[58] Field of Search ....................... 128/660.01, 660.07, 128/660.09, 660.1, 662.03, 662.06

[56] References Cited

U.S. PATENT DOCUMENTS

| | | | |
|---|---|---|---|
| 4,316,390 | 2/1982 | Kretz | 128/660.07 |
| 4,391,282 | 7/1983 | Ando et al. | 128/660.1 |
| 4,794,931 | 1/1989 | Yock | 128/660.03 |
| 4,805,155 | 2/1989 | Shiraishi et al. | 128/660.1 X |
| 4,917,097 | 4/1990 | Proudian et al. | 128/662.06 |
| 5,000,185 | 3/1991 | Yock | 128/662.03 |
| 5,054,492 | 10/1991 | Scribner et al. | 128/660.09 X |
| 5,115,814 | 5/1992 | Griffith et al. | 128/662.06 |
| 5,127,409 | 7/1992 | Daigle | 128/660.07 |
| 5,131,397 | 7/1992 | Crowley | 128/662.06 |
| 5,176,141 | 1/1993 | Bom et al. | 128/662.06 |
| 5,186,177 | 2/1993 | O'Donnell et al. | 128/662.06 |
| 5,240,003 | 8/1993 | Lancee et al. | 128/660.06 |
| 5,243,988 | 9/1993 | Sieben et al. | 128/662.05 |
| 5,271,400 | 12/1993 | Dumoulin et al. | 128/653.2 |
| 5,271,402 | 12/1993 | Yeung et al. | 128/660.1 |
| 5,284,148 | 2/1994 | Dias et al. | 128/662.06 |
| 5,353,798 | 10/1994 | Sieben | 128/662.06 |
| 5,485,845 | 1/1996 | Verdonk et al. | 128/662.06 |

OTHER PUBLICATIONS

Bruce J. Kimura et al. "Intracoronary Ultrasound", 1994, vol. 1A(484), p. 173A, *JACC*.

Harm ten Hoff, "Scanning Mechanisms for Intravascular Ultrasound Imaging", 1993, Chapter 5 & 6, pp. 117–151, *Universiteitsdrukkerij Erasmus Universiteit Rotterdam* (The Netherlands).

Harm ten Hoff et al., "Imaging Artifacts in Mechanically Driven Ultrasound Catheters", 1989, vol. 4, pp. 195–199, *International J. of Cardiac Imaging*.

*Primary Examiner*—Francis Jaworski

[57] ABSTRACT

An ultrasound apparatus for imaging tissues from interior of a cavity in the body of a patient is disclosed. The apparatus includes a probe for entering the body to the cavity. The probe has a distal end for entering the body and a proximal end to extend outside the body. At the distal end of the probe is a transducer associated with a rotatable mechanism for transmitting sequential ultrasonic pulses as the rotatable mechanism rotates, forming an angular pattern of transmitted pulses. Ultrasonic energy reflected and scattered from the patient's body tissues is received by an transducer so that each pulse generates a received signal (RF-line). The apparatus has a mechanism for identifying the angular separation between the RF-lines by analyzing the RF-lines caused by reflection and scattering by the body tissues alone. In this way, any distortion caused by the difference between the transmitted angular pattern and the intended angular pattern, if present, can be determined and corrected.

22 Claims, 10 Drawing Sheets

ULTRASOUND SYSTEM WITH NONUNIFORM ROTATION CORRECTOR

FIELD OF INVENTION

The present invention relates to the generation of an Intravascular Ultrasound image from a mechanical rotating intravascular catheter. More particularly, the invention relates to techniques and apparatuses for generating IVUS images with a reduced amount of image distortion due to nonuniform angular separation of ultrasonic pulses transmitted from the catheter by measuring and compensating for such distortion.

BACKGROUND

Ultrasonic imaging is widely used in medicine. In particular, it can be used for making images, and thus aiding in the diagnosis of disease, from inside body cavities such as the vascular system. A probe containing an ultrasonic transducer is inserted into the body area to be imaged. The transducer transmits an acoustic pulse into the body tissues, and detects the reflections of the pulse at tissue boundaries due to differences in acoustic impedance, as well as the backscattered sound from acoustically heterogeneous tissue. The differing times taken for the transducer to receive the reflected and backscattered ultrasound correspond to differing distances of the tissues from the transducer. By stepping or sweeping the transducer through a set of selected angles, a two-dimensional ultrasound image corresponding to a map of the acoustic impedance boundaries and backscattering coefficients can be obtained. From this image, the condition of the body tissues can be determined. For example, the method of intravascular ultrasound (IVUS) sequentially transmits ultrasound pulses in equally spaced increments around all or part of a circle to obtain cross-sectional images of coronary arteries demonstrating areas of atherosclerotic plaque, calcification, etc.

Generally, there are two types of ultrasonic probes for IVUS imaging. The first type employs a synthetic aperture technique. For example, U.S. Pat. No. 4,917,097 (Proudian et al.) and U.S. Pat. No. 5,186,177 (O'Donnell et al.) teach how an ultrasonic pulse is transmitted in a particular direction from a transducer using the method of synthetic aperture. Generally, this involves the sequential excitation of selected elements in an array of transducer elements.

The second type of IVUS probe scans the tissue, for example, that of the coronary artery, by mechanical rotation of a mechanism to direct the ultrasonic pulses. The mechanically rotated type includes a few subclasses. In the first subclass, either a distal (remote from the operator) transducer or a mirror is rotated from the proximal end of the catheter by an extended drive shaft with a proximal motor (U.S. Pat. No. 4,794,931 (Yock) and U.S. Pat. No. 5,000,185 (Yock)). In the second subclass, the rotation is confined to the distal end, where either a miniature motor (U.S. Pat. No. 5,240,003 (Lancee et al.) and U.S. Pat. No. 5,176,141 (Bom et al.)) or a fluid driven turbine is used to rotate the transducer or the mirror (U.S. Pat. No. 5,271,402 (Yeung and Dias)). In a third subclass, a stationary proximal transducer is acoustically coupled to a rotating acoustic waveguide that conducts the sound to the distal end (e.g., U.S. Pat. No. 5,284,148 (Dias and Melton). In a fourth subclass (e.g., U.S. Pat. No. 5,509,418 (Lum et al.)), a turbine is rotated by an acoustic signal generated outside the vessel to direct another ultrasonic signal in a rotating fashion. In the final subclass (e.g., U.S. Pat. No. 5,507,294 (Lum et al.)) an external driving member rotates a tube to rotate a reflecting element at the tip of the tube to reflect ultrasound.

Presently, probes that direct ultrasonic pulses by mechanical rotation are more widely used than the type of probes that electronically aim the pulses. The mechanical approach can be implemented using a single transducer, while the electronic approach requires an array of transducers to be contained in the distal end, which must pass into the blood vessel of interest.

However, one concern in the use of an IVUS probe with mechanical rotation is that the angular velocity of the rotating structure that directs the ultrasonic pulses may be nonuniform. Consequently, if ultrasound pulses are sequentially transmitted at uniform temporal intervals (as is usually the case), then the directions will be nonuniformly spatially distributed. A nonuniform angular velocity will thus distort the image that is formed. See, e.g., ten Hoff et al. *Int. J. Card. Imaging*, 4:195–199 (1989); Kimura et al., *JACC*, February 1994: 1A-484A, P. 173, Abstract No. 744-1. Kimura et al., supra, imaged a phantom that contained eight wires placed evenly in a circular pattern. In the displayed image, the angular separations between wires ranged from 10.2° to 73.9°.

One cause of nonuniform angular velocity in the type of catheter that uses a driveshaft is the existence of mechanical friction between the spinning driveshaft and the surrounding stationary sheath as they bend through the tortuous path of the blood vessel. Although the proximal end of the catheter is rotating at the desired angular velocity, any binding of the catheter along its length will lead to a distal angular velocity that is different from the desired velocity at various points of the full circle. The average velocity will be the same at the proximal and distal ends, and thus the distal end will sometimes be rotating too quickly, and sometimes too slowly. It has been observed, by ten Hoff, Kimura, and others that the error is substantially the same on subsequent revolutions of the catheter. Thus, the reflected ultrasonic energy that is received from a particular location will be portrayed in the resulting image as being from an incorrect location.

H. ten Hoff, in a thesis entitled "Scanning Mechanisms for Intravascular Ultrasound Imaging: A Flexible Approach," Erasmus University, Rotterdam, 1993, describes various techniques for detecting nonuniform angular velocity in rotating IVUS transducers and for correcting for distortion in images. Drawbacks in using acoustic methods for detecting and correcting for image distortion were identified by ten Hoff to include low resolution of ultrasonic reflecting structures, multiple reflection, and shadowing.

U.S. Pat. No. 5,485,845 (Verdonk et al.) describes a technique for detecting nonuniform angular velocity of IVUS transducers by using an array of beacons positioned on the sheath. However, this method requires special catheters with delicate structural features added to them. What is needed is a technique for detecting and correcting for nonuniform angular velocity using standard IVUS catheters.

SUMMARY

The techniques of the present invention rely on the changes that occur in the signals used to form the IVUS image, when the angular velocity of the transducer changes, to detect such nonuniform angular velocity and the image distortion it causes. The present invention provides an ultrasound apparatus for imaging from the interior of a cavity in the body of a patient. The ultrasound apparatus includes a probe for entering the body to the cavity. In the probe is a transducer for sequentially radiating from the probe's distal end ultrasonic pulses to form an angular pattern and for receiving ultrasound reflected and backscattered from the tissues of the patient's body. The apparatus also has an angle-identification mechanism for determining the angular pattern based on the ultrasound signals received by the transducer at the distal end of the probe.

The transducer transmits the ultrasonic pulses such that each ultrasonic pulse generates an ultrasonic signal reflected and backscattered from the tissues of the patient's body back to the transducer. The transducer then converts this ultrasonic signal to an electrical signal, commonly known as an RF-line. The angle-identification mechanism is capable of determining the angular pattern by analyzing these RF-lines alone. An example of such an angle-identification mechanism is a computer.

The present technique thus uses the ultrasonic signals that are otherwise present for the purpose of image acquisition for the additional purpose of determining the angular separation of the transmitted ultrasonic pulses. From this angular separation, and a knowledge of the times at which pulses are transmitted, this technique can further determine the angular velocity of the rotating mechanism (e.g., transducer or reflector) that directs the ultrasonic pulses. No additional physical structures in the probe or inserted into the body cavity, other than those already necessary for generating the image, are necessary for detecting nonuniformity of the angular separation. The great advantage of this technique, compared to prior art techniques, is that no modification is necessary to the probe. Therefore, any probe, even those currently being manufactured, will produce signals amenable to the treatment described, resulting in images with reduced distortion. In many cases, the present invention can be advantageously used to result in images in which the distortion would be substantially unnoticeable by human observers.

The present technique can be used to image from inside a variety of cavities, channels, etc, even of nonphysiological structure. A particular application of this invention is in intravascular ultrasound imaging using mechanical rotation. In this case, the probe is a catheter carrying a transducer on its distal end, and the tissues being imaged are those of the vascular system.

BRIEF DESCRIPTION OF THE DRAWINGS

The following figures are included to better illustrate the embodiments of the present invention. In these figures, like numerals represent like features in the several views.

DETAILED DESCRIPTION OF THE INVENTION

This invention detects image distortion due to nonuniform angular velocity of a transducer in a mechanical rotating type of IVUS catheter, and the subsequent nonuniform angular separation of the transmitted ultrasonic pulses. Only the signals reflected or scattered from the imaged tissues need be analyzed. No additional features are needed in the catheter or in the blood vessel.

Figure 1:
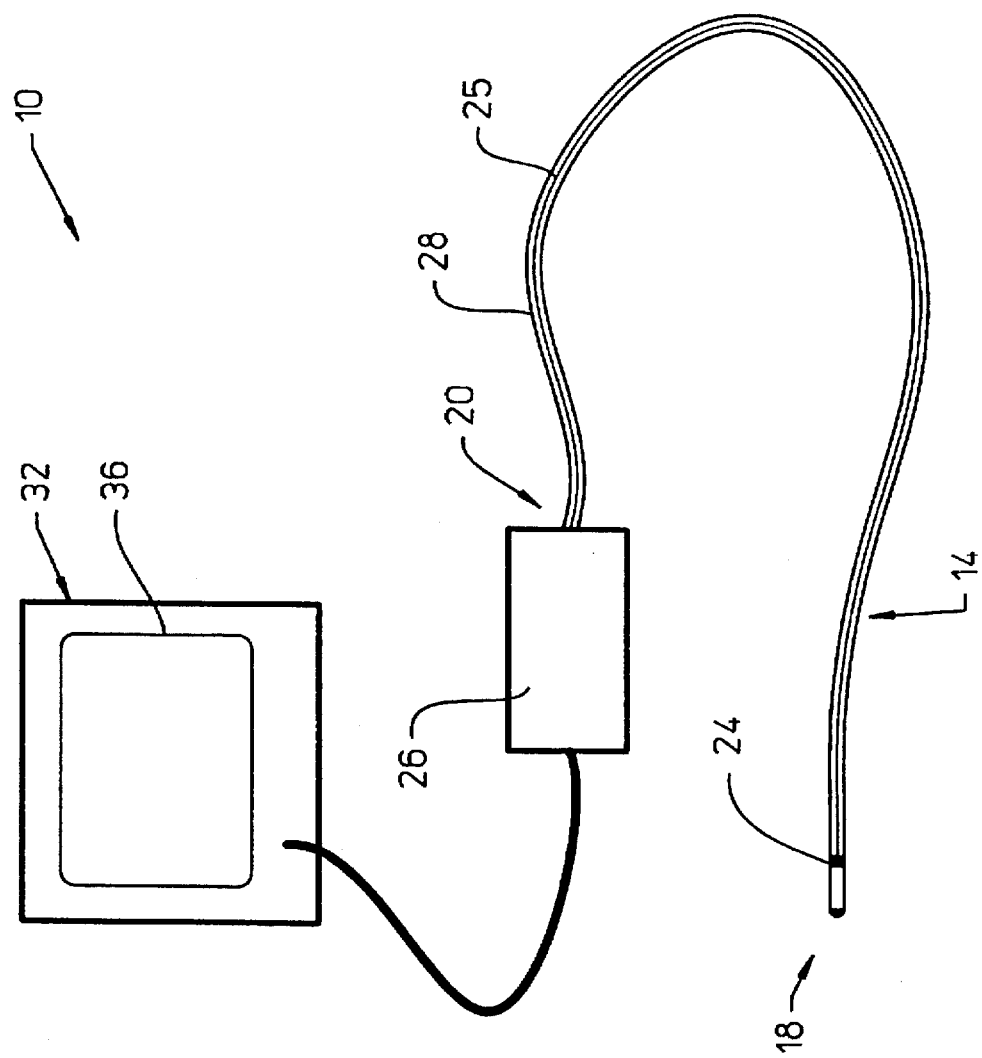
FIG. 1 shows a schematic representation of the ultrasound imaging apparatus of the present invention.

FIG. 1 is a schematic representation of the ultrasound imaging apparatus of the present invention. The apparatus can be used for imaging from inside a cavity, e.g., a blood vessel, in the body of a patient. The imaging apparatus 10 has a probe 14 for entering the body. The probe 14 has a distal end 18 for extend into the body cavity and a proximal end 20 that extends outside the body of the patient when the probe is in operation. The probe 14 includes at its distal end 18 a transducer 24 for transmitting and receiving ultrasonic signal. If desired, the same transducer, or different transducers, can be used for transmitting and receiving the ultrasonic signals. A shaft 25 powered by a motor 26 mechanically rotates the transducer 24 in the probe 14. The shaft 25, as well as the transducer 24, are protected inside a sheath 28 so that the shaft and transducer will not damage any tissue as the shaft rotates.

To image the tissue surrounding the probe 14, the transducer 24 radiates, or transmits, ultrasonic pulses in a sequential manner with an intended (i.e., target) angular pattern of angular separation between pulses. A controller 32 controls the rotation of the shaft 25 and the timing of the emission of ultrasonic pulses by the transducer 24. The transmitted ultrasonic pulses are reflected and scattered by the tissues. The reflections are received by the transducer 24, forming electronic signals (RF-lines).

The RF-lines are then analyzed by the controller 32 to determine the angular spacing, i.e., separation, of the RF-lines and subsequently compensate for the difference between the transmitted angular pattern and the intended angular pattern. In the case when the intended angular separation is uniform, such a difference, if uncorrected or uncompensated for, will result in nonuniformity and cause a distortion in the image of tissues. Of course, if a specific nonuniform angular pattern of ultrasonic pulses is intended, the present technique can be adapted equally well to detect and compensate for deviation of the transmitted pattern from the intended pattern. The corrected image can be shown on a display device 36, e.g., a television screen, monitor, printer, plotter, and the like. Instead of using a single controller 32 to control the rotation of the shaft, the transmission of the ultrasonic pulses, the analysis of data, and the implementation of the compensating measure to correct the distortion, different controllers and processors can be used, as long as they are coordinated to function in harmony.

Figure 2:
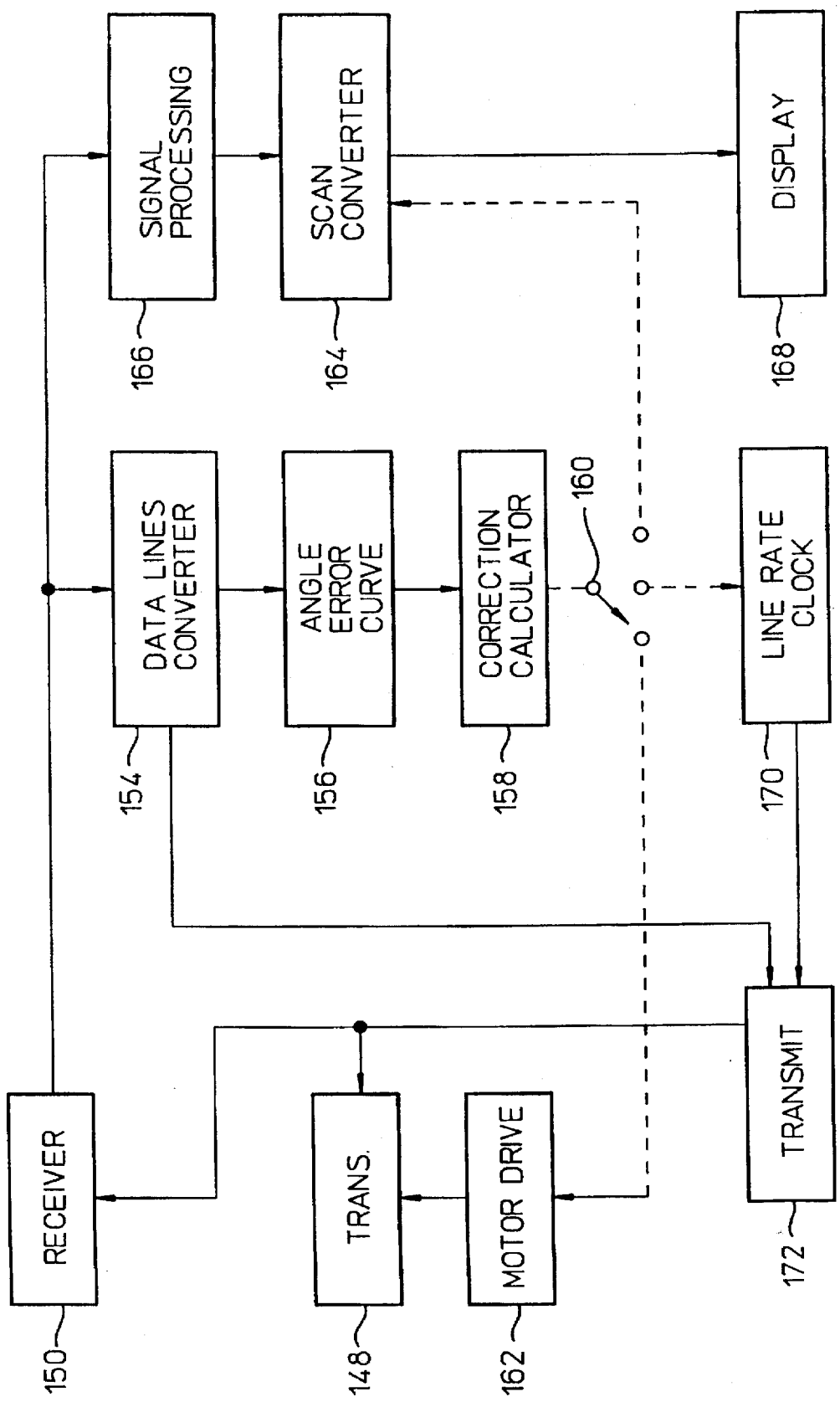
FIG. 2 shows a schematic representation of an embodiment of the controlling mechanism of FIG. 1 in a block diagram.

FIG. 2 shows a schematic of an embodiment of the controlling mechanism of FIG. 1 in a block diagram. Ultrasound is reflected and scattered from the tissue, then received by the transducer 148, and converted to an electrical signal (known as an RF-line), which signal is passed to the receiver 150. A RF-line is therefore an electrical representation of the acoustic pressure signal seen by the transducer. The RF-lines pass from the receiver 150 to a data line converter 154 to maintain or convert, such as by demodulation, to a selected type of data lines that reflect a particular characteristic of the RF-lines, e.g., amplitude-lines, phase lines, baseband lines, and the like. A baseband line is the complex electrical signal that is generated by the frequency shifting of the RF-line by its center frequency, nominally the frequency of the transmitted pulse. This signal is generated by, for example, multiplication by in phase and quadrature representations of a sinusoid at said center frequency, followed by lowpass filtering. In the following, we will commonly refer to angular separation of data lines, be they RF-lines or any of the derivative forms. It is to be understood that such reference refers to the angular separation of the ultrasonic pulses that are received and from which the data lines are derived.

The data line converter passes the data lines to the angle error curve module 156 to calculate the angular separation of the RF-lines, and thus the angular separation error curve of the rotation of the transducer 148. The angular error curve data is passed from the angle error curve module 156 to a line rate correction module (or calculator) 158. The line rate correction module 158 is capable of providing compensation for nonuniform angular velocity by any of the methods and techniques described by Verdonk, et al. Such techniques by Verdonk et al. are incorporated by reference herein. Depending on the position of the switch 160, the correction calculator 158 will either (a) vary the speed of the motor to change the velocity of rotation, (b) vary the algorithm in the scan converter 164 to modify the image shown in a display 168, or (c) control the line rate clock 170 to transmit via transmitter 172 at such a rate as to result in a distortion-free image. It is to be understood that the embodiment is shown as an illustration only. One skilled in the art will know that some of the blocks in FIG. 2 can be combined, or subdivided into more blocks, either as electronic circuits, or as computer program functional blocks, to perform essentially the same function.

Backscattered Signals

As noted above, the signal observed when forming an ultrasound image may be decomposed into two components: (1) reflections from boundaries between materials with different acoustic properties—these signals are known as specular reflections; and (2) scattering from materials whose composition is a heterogeneous mixture of components with different acoustic properties. The heterogeneity of the material is on a scale that is small compared to a single wavelength of the insonating ultrasound. This kind of signal is known as backscattered signal. Most of the tissues of the human body (as well as other mammalian bodies) generate backscattered signal, with specular reflections arising from boundaries between tissues.

The ultrasonic pulse used to generate the backscattered signal has a finite pulse length, and has finite width. Thus, the received signal (i.e., RF-line) depends on the addition of backscattered ultrasound waves from very many randomly positioned scatterers (i.e., individual elements in the tissue that cause detectable backscattered signal), with the result that, at some particular time, constructive or destructive interference may occur. The amplitude and phase of the received signal thus fluctuates randomly. When the amplitude information is converted to form an image, this randomness leads to the characteristic speckled appearance of ultrasound images.

Further, if one measures signal backscattered from two regions, the measurements will become highly correlated as the distance between the two regions becomes smaller than the size of the ultrasonic pulse. Thus, although the particular speckle pattern observed depends on the precise distribution of scatterers, many of its properties depend more strongly on the ultrasonic pulse dimensions than on the exact details of the insonified tissue. In particular, the size of the speckle cells and many other statistical information derived from measurements in speckle regions of an image depend on the pulse characteristics.

How the Angular Velocity of the Transducer is Measured

Consider a series of RF-lines acquired from reflecting and scattering sequential ultrasonic pulses. In a mechanically rotating catheter, this should correspond to angular separation of the RF-lines. In a speckle-producing tissue, at any given range, one expects the RF-lines to remain correlated over an angle corresponding to the angular width of the pulses. The RF-lines will become decorrelated only after a pulse insonates an entirely new set of scatterers relative to other RF-lines. That is, the RF-lines will become decorrelated at any particular range only when the corresponding pulses do not overlap.

This invention uses the variation with angle of the statistical properties of the RF-lines, which are otherwise used to form the image, to provide an estimate of the angular separation of these RF-lines. That is, by measuring certain characteristics of the speckle, the angular separation of the lines is determined. The input data to the method of analysis can be any data lines derived from the acquired RF-lines; such as the RF-lines themselves; the complex baseband lines formed by downconversion of the RF-lines i.e. downshifting by the frequency of transmitted pulse so that the RF-lines now center about zero frequency instead of centering about the frequency of the transmitted pulse; the A-lines (amplitude lines) that are formed from the RF-lines by envelope detection or another demodulation scheme; the phase lines formed by detecting the phase of the RF-lines; or the IVUS image itself formed by scan-converting the A-lines from an r-theta format to a x-y format suitable for display on a computer screen. The preferred input is, however, the RF-lines or baseband lines. From such data, other possible inputs can be easily derived by one skilled in the art.

From a measurement of the angular separation of the RF-lines, one can deduce the angular velocity of the catheter, and thus measure the nonuniformity of that velocity, i.e., the deviation of the angular velocity from the intended (or target) velocity. The methods discussed in the U.S. Pat. No. 5,485,845 (Verdonk, et al.) may then be applied to correct for the nonuniformity or deviation from the intended pattern to produce an image free from distortion.

Many different methods of calculations can be used to derive the angular separation of RF-lines. Here we describe three such methods, though others will be obvious to those skilled in the art based on these illustrative methods. In these methods, we measure the relative separation of the RF-lines and normalize to obtain the absolute angular separation between the RF-lines.

The Cross-Product Calculation

This method uses the normalized cross-product of data lines, such as RF-lines, phase-lines, etc., as a measure of the angular separation of the RF-lines. For illustration purposes, here we specifically choose the complex baseband lines obtained from the RF-lines by downconversion as an example for the data lines. Denote a particular baseband line by $a_p$, where p specifies the particular baseband line we are interested in and a is the quantity of that line. Since data are collected as discrete samples, denote the samples of $a_p$ as $\{s_p(1), s_p(2), \ldots, s_p(n)\}$. Denote the subsequent baseband line by $a_{p+1}$, consisting of samples $\{s_{p+1}(1), S_{p+1}(2), \ldots, s_{p+1}(n)\}$. The normalized cross-product of the baseband lines $a_p$ and $a_{p+1}$ is:

$$C_{p,p+1} = \frac{\sqrt{\sum_{m=1}^{n} |s_p(m) \cdot s_{p+1}^*(m)|}}{\sqrt{\sum_{m=1}^{n} |s_p(m) \cdot s_p^*(m)|}} \quad \text{Eq. 1}$$

where * denotes complex conjugation, n is the number of samples and m is an arbitrary integer variable for performing the summation over n. The corresponding cross-product sums $C_{p,p+2}$, $C_{p,p+3}$, etc., between baseband lines p,p+2, and p+3, etc., can be calculated using the following baseband lines $a_{p+2}$, $a_{p+3}$, etc. Similarly, the preceding lines can be used to form $C_{p,p-1}$, $C_{p,p-2}$, $C_{p,p-3}$, etc. From the correlation properties described above, we have the relationship $E(C_{p,p+1})$, $E(C_{p,p-1}) > E(C_{p,p+2})$, $E(C_{p,p-2}) > E(C_{p,p+3})$, $E(C_{p,p-3})$ etc., where E denotes the expectation in the statistical sense. Depending on the beam width (i.e., the angle over which the pulse spreads) and separation of the data lines, the expected value of the cross product of two lines eventually falls to some minimum value, determined by the noise level in the system, as the two data lines become further separated from each other. Thus, we can assign a width to the cross-product of one particular data line with its neighbors.

An appropriate measure of the width might be the number of lines required for the cross-product to drop to one-half of its peak value, though other measures will be obvious to those skilled in the art. For example, if RF-lines are acquired with a 1° spacing, and the beam width is 5°, then the cross product should reach a minimum at $E(C_{p,p+5})$, assuming that the angular separation of pulses is uniform. The same process can be repeated for each RF-line, to calculate $C_{p+1,p+2}$, etc.

If the transducer is rotating at a uniform angular velocity, so that the RF-lines are equally spaced, then the width of the cross-product should remain the same for all RF-lines. If the transducer rotates faster than expected over some sector of the full circle, then the RF-lines will be spaced further apart than otherwise, and the width of the cross-product function, measured by the number of data lines required for its value to fall as described above, will be smaller than normal. On the other hand, if the transducer rotates more slowly than normal, the RF-lines will be spaced closer together, and the cross-product width will consequently increase.

The relationship between cross-product width and angular velocity is inverse linear. By calculating the cross-product width, either in software or via dedicated hardware circuitry, the nonuniformity of the transducer rotation, and thus of the data line angular separation, can be measured, and separately corrected by the methods described in the Verdonk patent. For example, if it is found that at some particular line the angular velocity is greater than desired, the firing rate of the transducer can be increased at that angle of rotation to compensate for the faster rotation, such that the RF-lines are evenly spaced in the resulting image. The other methods of compensating described by Verdonk et al., supra, can also be used.

Normalization

Normalization is an operation performed by adding up the measured separations and relate them to the actual angle of rotation. For example, for the cross-product method, one adds together the reciprocals of all the measured widths, dividing each of the individual separations by the total, then multiplies each by the correct total angle. In this way, the correct total separation will result, and each individual measured separation is now known absolutely rather than relatively. For a particular pulse shape (as produced by, e.g., a particular design of the transducer), a calibration curve may be provided a relationship of, e.g., cross product width to absolute angular separation. If such a curve is provided, then normalization becomes unnecessary. Normalization can be used for the following methods as well. In all of the methods of determining similarity between data lines described in this disclosure, the measure of angular separation is normalized so that the sum of the separations adds up to the correct total angle. In the case of IVUS, where the image is usually of a full revolution, the sum of the separation angles must add up to 360°.

Difference Calculation

This method of calculation uses the normalized difference between data lines, such as RF-lines, A-lines, baseband lines, etc., as a measure of the separation of the RF-lines. Consider the example of using the baseband lines as data lines for this analysis, using the same notations as in the cross-product calculation above, the normalized line-to line root mean square difference for line $a_p$ from line $a_{p+1}$ is:

$$RMS\, D_{p,p+1} = \frac{\sqrt{\sum_{m=1}^{n} |s_p(m) - s_{p+1}(m)|^2}}{\sqrt{\sum_{m=1}^{n} |s_p m|^2}} \quad \text{Eq. 2}$$

If the transducer is rotating more slowly than normal, the difference will become small, since the lines will become more similar, due to greater commonality in the scatterers that generate the RF-line. If the transducer is rotating more rapidly than normal, then the difference will become large.

The root-mean-square difference is shown in Eq. 2 above. However, other kind of differences can be used, for example, the mean-square-difference $$MSD_{p,p+1} = \frac{\sum_{m=1}^{n} |s_p(m) - s_{p+1}(m)|^2}{\sum_{m=1}^{n} |s_p m|^2} \quad \text{Eq. 3}$$

and even the simple difference $$D_{p,p+1} = \frac{\sum_{m=1}^{n} |s_p(m) - s_{p+1}(m)|}{\sum_{m=1}^{n} |s_p m|} \quad \text{Eq. 4}$$

A person skilled in the art will be able to derive other differences for this analysis. By calculating the RF-line-to-line difference, using either software or dedicated hardware circuitry, the nonuniformity of transducer angular velocity can be measured and corrected by techniques similar to those described above.

As previously stated, in the cross-product calculation there is an inverse linear relationship between cross-product function width and angular velocity. However, in the present difference method there is a direct relationship, wherein a greater difference implies greater angular velocity. However, the exact nature of the relationship depends on the pulse profile produced by a particular transducer. Calibration curves relating the difference to angular velocity can be used to evaluate the angular velocity.

Cell Size Variation Calculation

This method analyzes the size of the speckle cells themselves. The following steps are taken:

1. First, a technique for defining a speckle cell is selected. For example, take the amplitude of each sample, then consider all the neighboring samples whose amplitude is sufficiently similar to belong in the same speckle cell. An alternative is to take the phase of each sample of the baseband lines signal, then consider all the neighboring samples whose phase shift relative to the first sample is less than a set amount, e.g., 90°, to belong to the same speckle cell. Even more simply, the phase could be quantized to a single bit, and then speckle cells be defined by regions in which this one bit is constant. Based on the present disclosure, other methods of defining a speckle cell are obvious to one skilled in the art.

2. Now consider each sample along a data line, and measure the size of the speckle cell in which it lies, measured along the angular direction. The result of this process is a distribution of speckle cell sizes for each line.

3. Calculate a set of appropriate statistics, such as the average, from the distribution of speckle cell sizes to determine the angular velocity for each line. If the catheter is rotating more slowly than normal, then the increase in similarity between lines will cause the speckle cells to increase in size. This increase is reflected in the distribution of cell sizes, e.g., the average cell size will increase. Similarly, for an increase in velocity, the average cell size will decrease. This method, like the cross-product method, results in an inverse linear relationship between velocity and speckle cell size.

It is noted that, as in the speckle cell method, the phase or the amplitude of the RF-lines can be analyzed in the cross-product method and in the difference method as well. The important aspect is to determine the change of the particular characteristic, i.e., amplitude, phase, or combination thereof, of one RF-line relating to other RF-lines, as one moves from RF-line to RF-line, to determine angular separation between RF-lines.

Enhancements

A possible difficulty with analyzing RF-lines alone to detect nonuniform angular velocity is that the tissue being insonified has structures which generate long range coherence, usually referred to as specular reflectors. For example, a vessel might contain a lesion containing calcification, which will have a substantially different reflectivity than the tissue of the vessel wall. There may also be structures present which provide specular reflections. The cross-product of data lines derived from RF-lines in tissues that contain such structures may be large even when the angular separation is such that the beams do not overlap. This will lead to an underestimation of the angular velocity of the transducer. Similar errors will occur for the other methods described.

One way to alleviate these difficulties is to restrict the depth range over which the cross-product is calculated to ensure that signals from backscatter predominate over signals from specular reflectors. This can be done, e.g., by using signal only from the blood immediately surrounding the catheter (in the case of IVUS); by using signal only from that region that lies beyond the internal elastic lamina (to remove the effect of the blood/wall interface echo); and the like.

Another way is to employ a method that reduces the influence of the large amplitude signals coming from specular reflections. For example, one can severely clip the signal amplitude, or use the signal phase alone, or perhaps simply use the sign of the signal phase (which is equivalent to a 1-bit quantization of the phase). Such simplifications also lead to extremely fast calculation circuits, allowing the methods described above to be implemented in real time.

A further difficultly arises if the ultrasonic pulse used is extremely narrow in the angular direction, because there maybe little or no overlap in the scatterers insonated by neighboring ultrasonic pulses. In this situation, the cross-product function width is zero, and no information on angular separation is available. This problem can be solved by increasing the rate of production of RF-lines. For an imaging depth of 2 cm, only about 30 μs is required for each RF-line. At a frame rate of 30 Hz, this allows over 1000 RF-lines to be transmitted per revolution. Thus, in this embodiment, considerable angular overlap is provided for any foreseeable intravascular transducer. In addition, for the preferred correction method of Verdonk et al, in which the timing of the transmission of pulses is changed to compensate for the nonuniform angular velocity of the probe, uniformly spaced data lines will be acquired once sufficient correction is applied. As a result, we require only that data lines overlap when uniformly spaced, rather than overlap for the highest conceivable rotational velocity.

EXAMPLES

Figure 3:
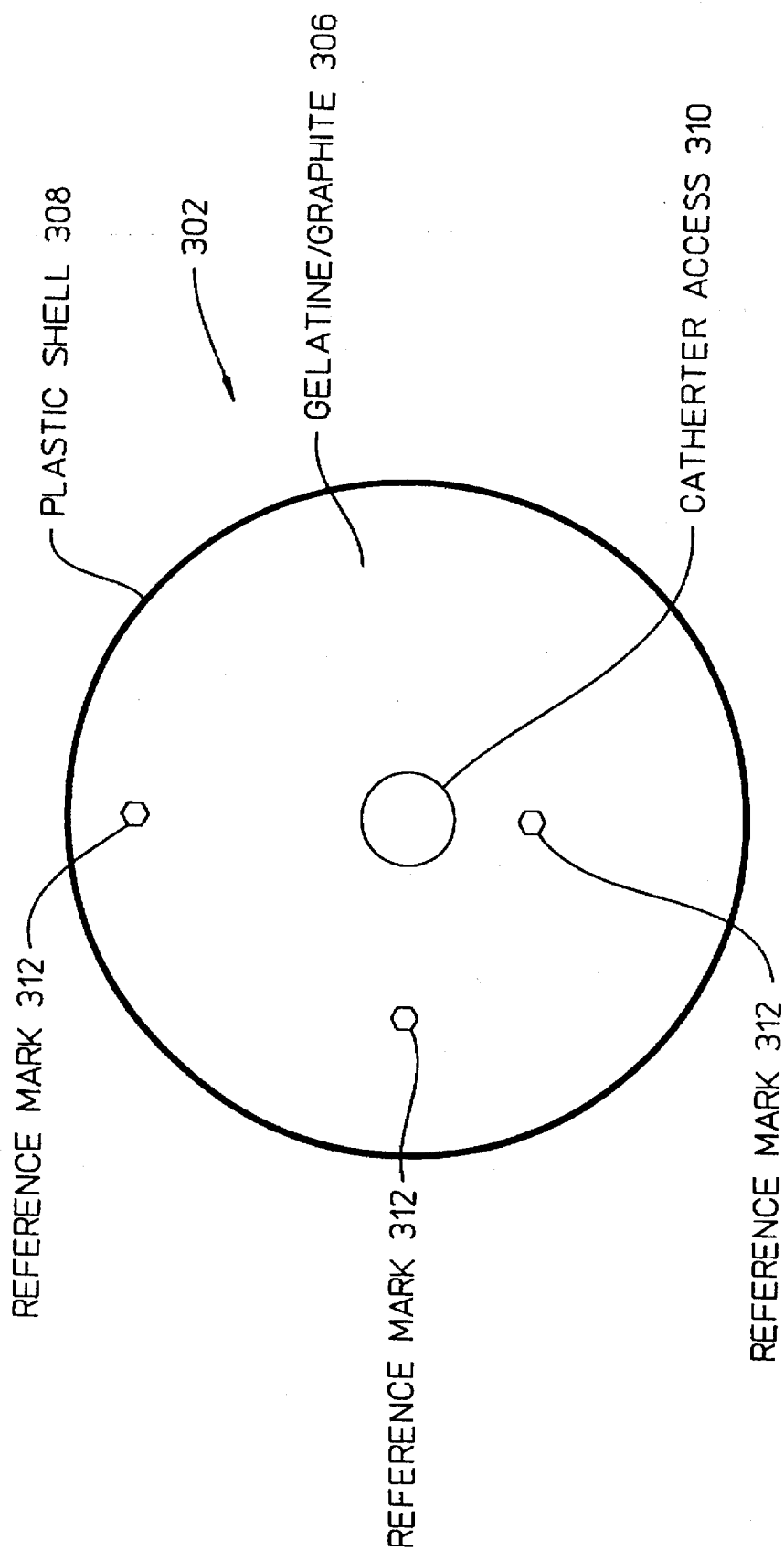
FIG. 3 shows the apparatus used in creating RF-lines from ultrasonic pulses that are not uniformly separated, using a rotating phantom and a stationary IVUS catheter.

To evaluate each of the three methods described above, an apparatus was constructed that allowed an IVUS catheter to be used in such a manner that a phantom could be rotated about the catheter in a controlled manner while the catheter does not rotate. By this method, one can simulate any nonuniformity of separation of data lines. FIG. 3 shows such a system.

The system 340 included the IVUS imaging system (HP SONOS 100) 342 with a catheter 344. A digital data acquisition oscilloscope 346, e.g., running at 250 MHz (i.e., sampling at 250M samples per second), was used to collect data from the IVUS imaging system 342. The transducer 350 was positioned inside a phantom 352. The phantom 352 was rotated by the stepper motor 354, which was controlled by the control computer 356 based on a predetermined (target) angular rotation pattern. The data acquisition oscilloscope 346 was connected to the RF Data Port and Envelope Data Port on the IVUS imaging system 342. In this way, RF-lines and A-lines could be collected and stored in a computer file. The data were analyzed with a computer program, although in a practical implementation a dedicated hardware circuit could be used.

Figure 4:
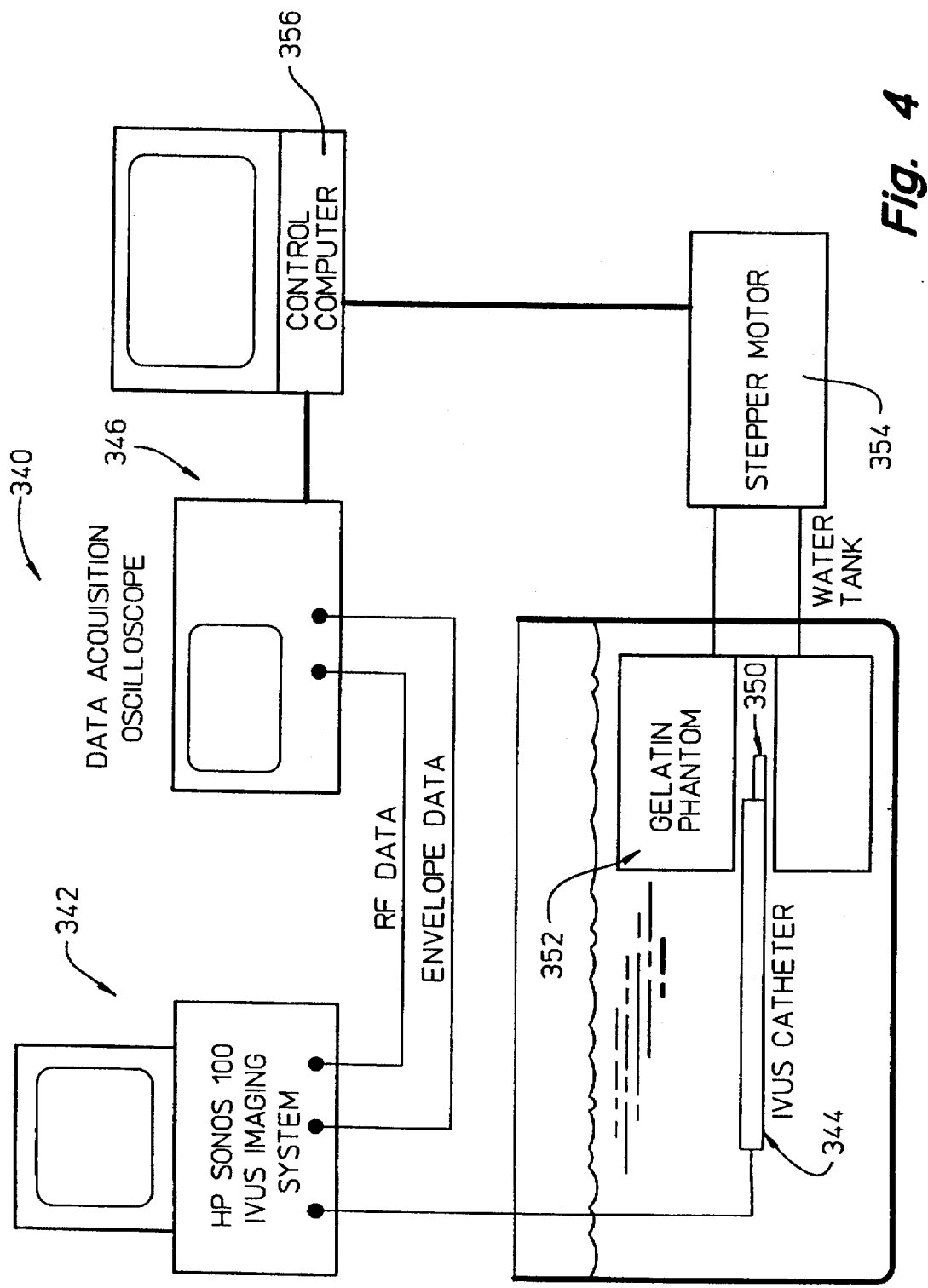
FIG. 4 shows a cross-sectional view of the phantom used in the apparatus of FIG. 3.

A phantom 302, whose cross section is shown in FIG. 4, was constructed from gelatin with graphite scatterers 306 and had a plastic shell 308. This phantom contained a central hole 310, in which the IVUS transducer could be inserted, and a number of reference markers 312 that allowed observation of nonuniformity of rotation. The markers 312 were positioned with 90° spacing relative to the center of the phantom.

The phantom was attached to the stepper motor 354 controlled by the control computer 356. This allowed the phantom to be rotated to any particular angle under computer control. By appropriate choice of a set of angles, this system could be used to acquire an image identical to that which would be acquired by a standard IVUS system with any degree of nonuniform catheter rotation.

For effective calculation of the rotational velocity and compensation of nonuniformity, it is preferred that the RF-lines are about 1° to 2° apart for a catheter with a transducer rotating at about 30 cycles/second. For example, transmitted ultrasonic pulses, with a frequency of about 30 MHz and a duration of about 1 cycle, will provide adequate signal for calculation of changes, e.g., for calculation of cross-product, difference, speckle cell size change, between lines and for forming a corrected image with adequate clarity, for a 3.5 French, 1.5 meter long catheter.

Figure 5:
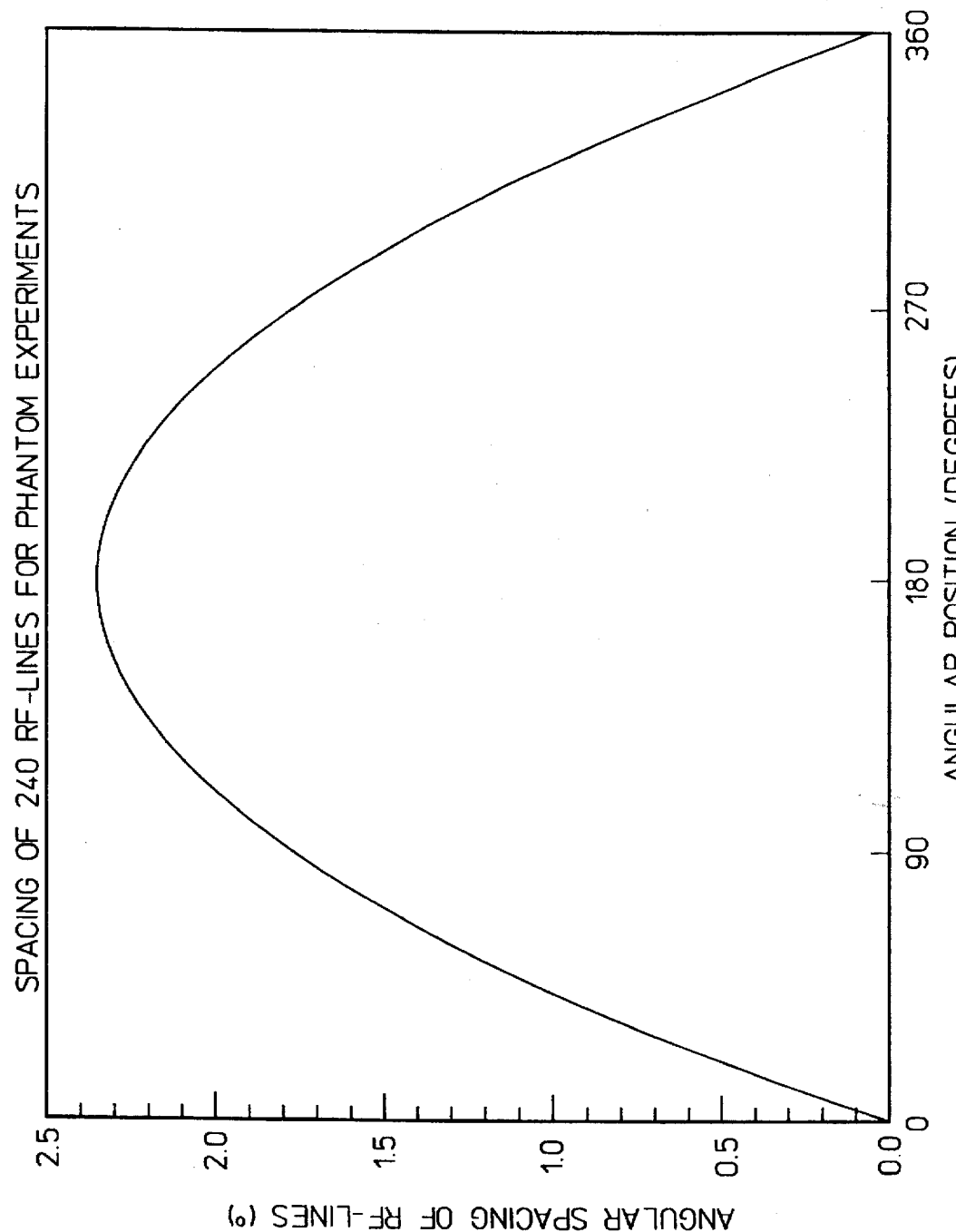
FIG. 5 shows the pattern of angular separation of ultrasonic pulses used to simulate nonuniform angular separation.

The control computer 356 was programmed to simulate nonuniform rotation such that the angular distance between data lines, as a function of angle, is as shown in FIG. 5. The abscissa shows the angular position around the axis of the phantom and the ordinate shows the angular separation of the RF-lines for the different angular positions on the phantom. The average separation of the 240 RF-lines is 1.5°, making a total of 360°. As seen in this figure, the lines are closely spaced at first (corresponding to a low velocity), then more widely spaced (corresponding to a higher angular velocity), then more closely spaced again for the remainder of the full rotation. In this way, the RF-lines obtained by the transducer receiving the reflected ultrasonic pulses have regions where there is substantial overlap of insonated scatterers, and regions where there is less overlap. On each of the angular separation estimate curves described hereinafter, i.e., in FIGS. 8, 9 and 10, the actual angular separation used is shown, as a dotted line, along with the estimate of that separation, shown as a solid line.

Figure 6:
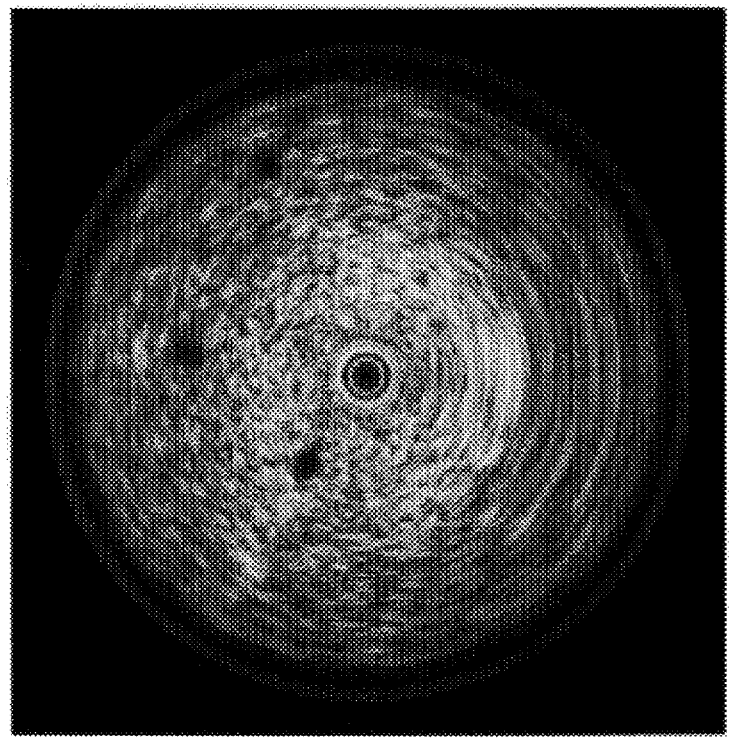
FIG. 6 shows an image obtained with the apparatus of FIG. 3, showing the result of uncorrected, nonuniform angular separation of ultrasonic pulses.

FIG. 6 shows the original image acquired without any correction for nonuniform angular separation. The image shown is scan-converted from the envelope signal from the data port output of the SONOS Imaging system. The reference holes are clearly not spaced at 90° intervals, indicating that severe nonuniformity of angular separation has occurred.

Figure 7:
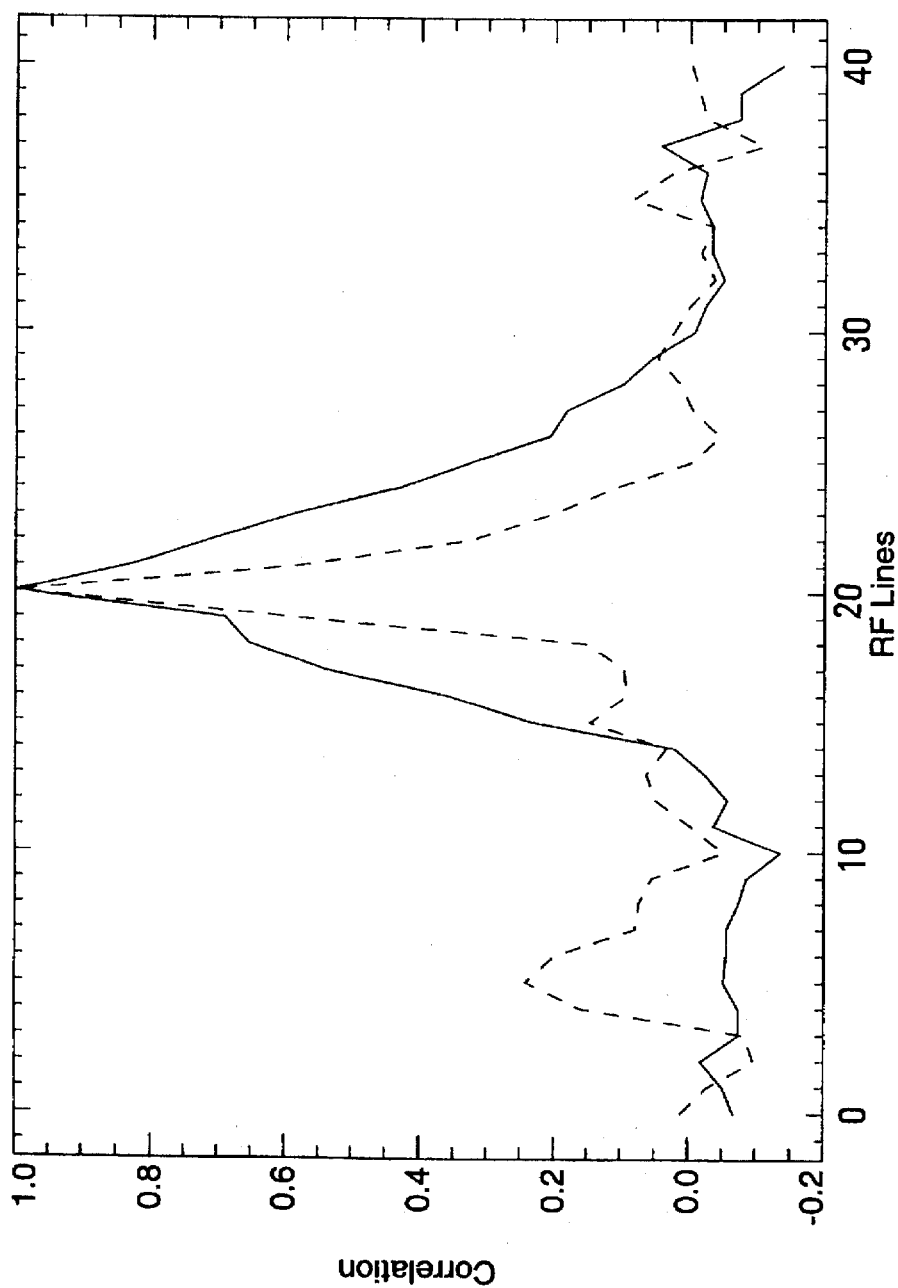
FIG. 7 shows a graphical representation of two examples of cross-product functions. The dotted line represents a cross-product function of a RF-line to its neighboring RF-lines in the region of wide angular separation of ultrasonic pulses and the solid line represents the cross-product function of a RF-line to its neighboring RF-lines in the region of small angular separation.

FIG. 7 shows the cross-product function for two RF-lines. The broad cross-product function (solid line in FIG. 7) corresponds to the small angular separation (seen at the 3 o'clock position in the image in FIG. 6); the narrow cross-product (dotted line in FIG. 7) corresponds to larger angular separation (seen at 9 o'clock in FIG. 6). The calculation was performed according to Equation 1, with the modification described wherein the cross-product is calculated between the sign of the phase of the baseband lines. That is, we used the one-bit quantized phase modification to the cross-product calculation.

Figure 8:
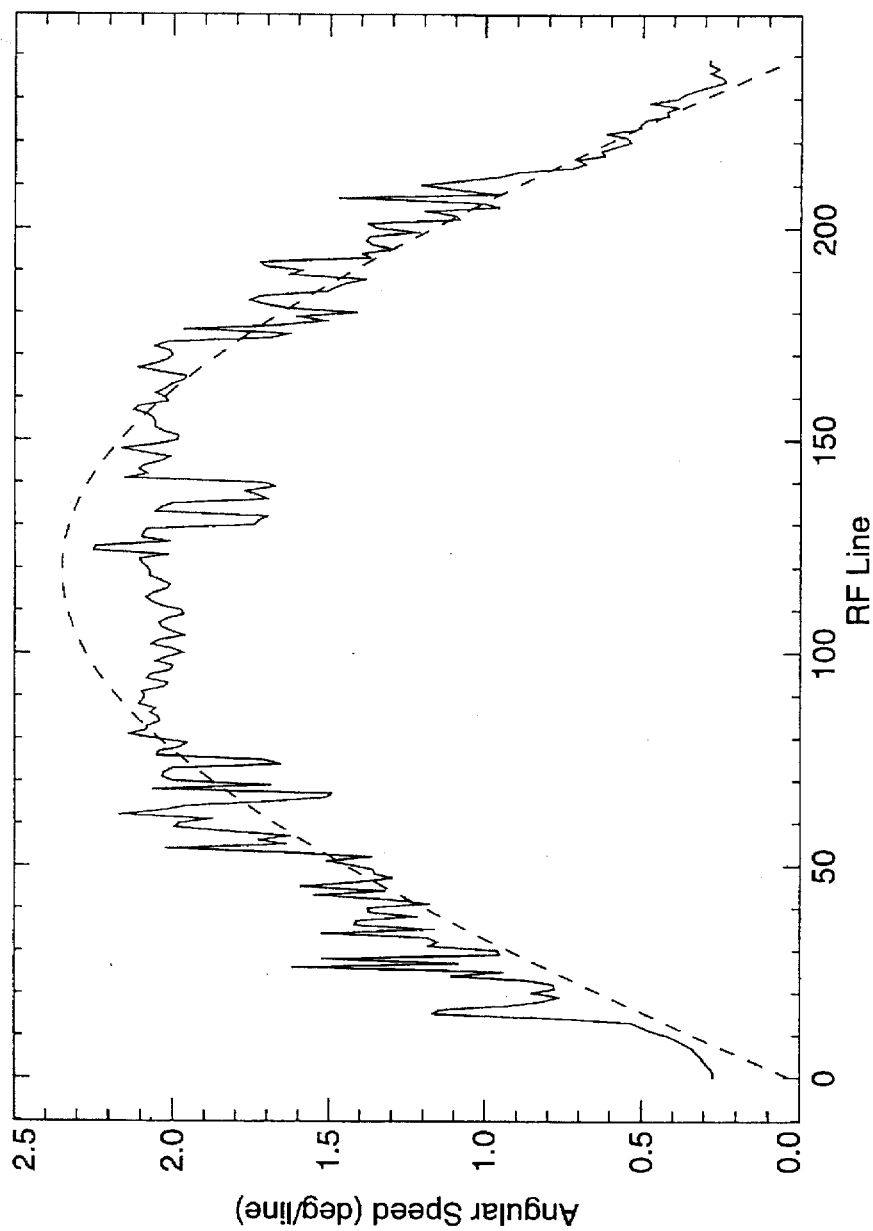
FIG. 8 shows a graphical representation of the estimated angular separation of ultrasonic pulses, in °/line, calculated using the cross-product method.
Figure 9:
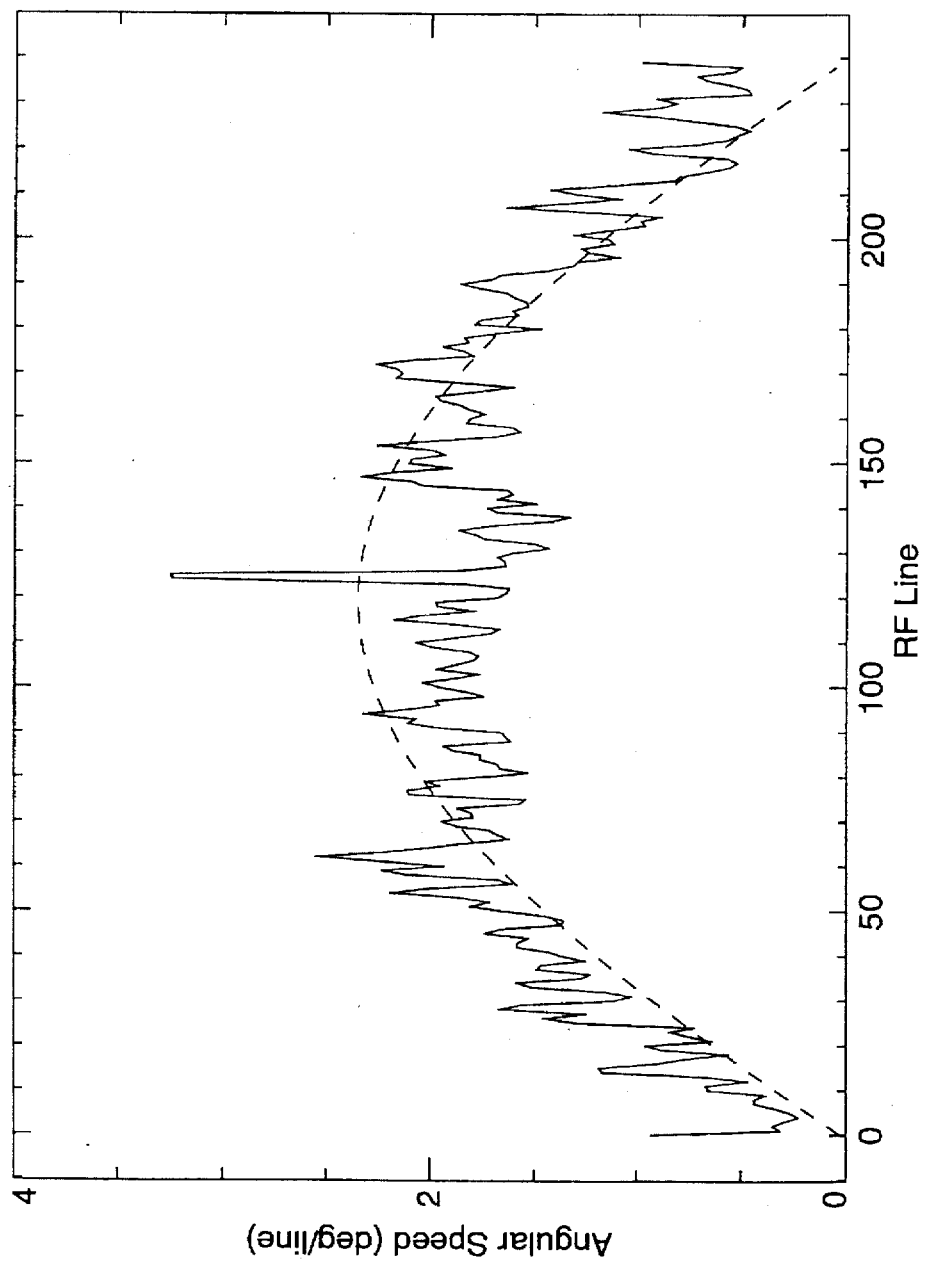
FIG. 9 shows a graphical representation of the estimated angular separation, in °/line, calculated using the difference method.

FIG. 8 shows, as the solid line, the angular separation of data lines estimated by the cross-product method described above. The dotted line shows the true angular separation of the data lines. FIG. 9 shows the velocity estimated by the difference calculation above, using the modification described wherein the difference used is that of the sign of the phase of the baseband lines.

Figure 10:
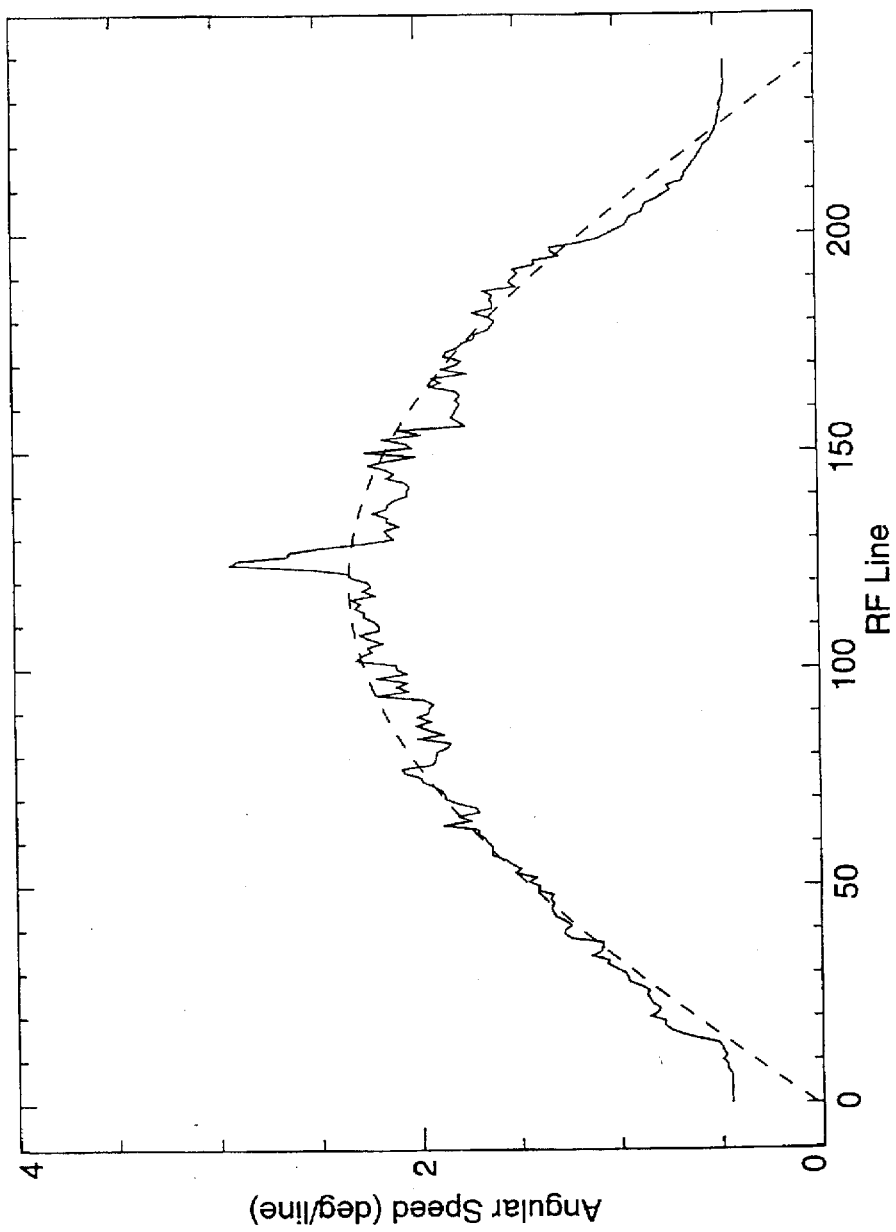
FIG. 10 shows a graphical representation of the estimated angular separation, in °/line, calculated using the speckle size method.

FIG. 10 shows the angular velocity estimated using the speckle cell size calculation described above. In this instance, the size of the speckle cell was defined to be the number of data-lines traversed in an angular direction before the phase of the baseband lines changes by more than 90°. The size was calculated for each sample of each baseband line, then the velocity was set proportional to the inverse of the average size, after discarding those sizes greater than one quarter of a full revolution.

Figure 11:
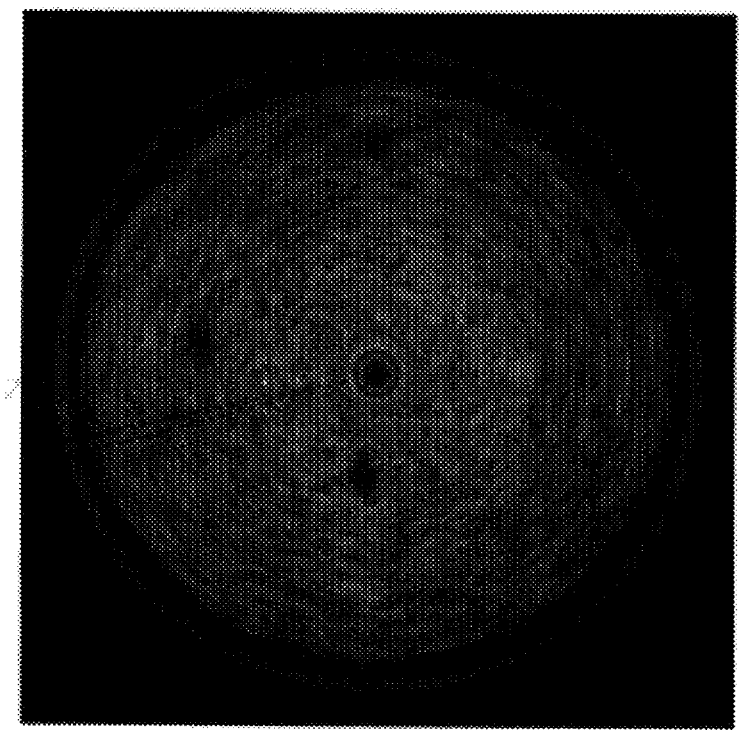
FIG. 11 shows a corrected image, using the angular separation estimate obtained by the speckle cell size method.

FIG. 11 shows an image corrected by scan-converting the data according to the measured separations, as described in Verdonk et al., using the same data used for forming the image in FIG. 6. Because the same data were used, the quality of the image in FIG. 11 suffers somewhat in regions where there is an insufficient density of RF-lines. For this reason, the modified firing rate method, an alternative way to correct the image during the next rotation of the catheter, is preferred. All of the methods of correction disclosed by Verdonk can be adapted for the present invention. Although the correction is performed on the rotation, firing rate, or scan-converting after the measurement, this works well for practical imaging purposes because the nonuniformity in angular velocity is quite repeatable from one revolution to the next. How pixels in a display, e.g., TV screen or monitor, are activated corresponding to data lines is known in the art and will not be described in this application.

It is to be understood that the example is given for illustration purposes only, and variations can be made by a person skilled in art, based on the present disclosure. For example, a reflector can be rotated to direct, i.e., reflect the ultrasonic pulses, instead of rotating the transducer. Further, it is to be understood that the technique to detect and correct for nonuniform angular velocity of the present invention can be applied in imaging structures surrounding a transducer other than a blood vessel. For example, the technique can be used to image from other body cavities, such as esophagus, gastrointestinal tract, uterus, bladder, and even from other cavities such as lumens in pipes and interior walls of holes in nonbiological structures.

What is claimed is:

1. An ultrasound apparatus for imaging tissues in the body of a patient from interior of a cavity in the body, comprising:

(a) a probe for entering the cavity, the probe having a distal end to extend into the cavity, a proximal end to extend outside the body, and including mechanical rotatable means including one or more transducers for transmitting sequential ultrasonic pulses in an angular pattern from the distal end based on a target angular pattern and for receiving ultrasonic energy reflected and scattered from the tissues back to the one or more transducers, such that each transmitted ultrasonic pulse results in a received signal (RF-line) converted from said reflected and scattered ultrasonic energy, said RF-line being subsequently used for forming a tissue image;

(b) angle-identification means for determining the transmitted angular pattern by analyzing the RF-lines to determine angular separation therebetween, said angle-identification means being capable of determining the transmitted angular pattern by analyzing the RF-lines alone; and (c) correction means for correcting distortion of the tissue image caused by the transmitted angular pattern being different from the target angular pattern.

2. The apparatus of claim 1 wherein the angle-identification means is adapted to determine the similarity between RF-lines to determine the angular separation between RF-lines, wherein a high degree of similarity indicates a small angular separation and a lesser degree of similarity indicates a greater separation, the angular separation between the RF-lines determining the transmitted angular pattern.

3. The apparatus of claim 2 wherein the angle-identification means is adapted to compare one data line to other data lines to determine the transmitted angular pattern, the data lines being derived from the RF-lines.

4. The apparatus of claim 3 wherein the angle-identification means is adapted to compare data lines derived from the RF-lines, said data lines being selected from RF-lines, RF amplitude lines, RF phase lines, baseband lines, baseband amplitude lines, baseband phase lines, quantized RF phases, and quantized baseband phases, to determine the transmitted angular pattern.

5. The apparatus of claim 4 wherein the angle-identification means is adapted to compare data lines derived from the RF-lines to determine the cross-product of the data lines to determine the transmitted angular pattern.

6. The apparatus of claim 4 wherein the angle-identification means is adapted to compare data lines by calculating the cross-product among data lines as $$C_{p,p+1} = \frac{\sqrt{\sum_{m=1}^{n} |s_p(m) \cdot s_{p+1}*(m)|}}{\sqrt{\sum_{m=1}^{n} |s_p(m) \cdot s_p*(m)|}} \quad \text{Eq. 1}$$

where * denotes complex conjugation, s is the magnitude of a sample in the data line, p represents the specific data line of interest, n is the number of samples in a data line, and m is an arbitrary integer variable of summation.

7. The apparatus of claim 4 wherein the transducer means angle-identification means is adapted to determine the transmitted angular pattern by analyzing differences between data lines.

8. The apparatus of claim 7 wherein the transducer means angle-identification means is adapted to determine the transmitted angular pattern by analyzing root means square difference between data lines.

9. The apparatus of claim 3 wherein the angle-identification means is adapted to determine the transmitted angular pattern by analyzing the data lines to define speckle cells each having generally uniform ultrasonic characteristics therein and analyzing consistency of the dimensions of the speckle cells between said data lines.

10. The apparatus of claim 1 wherein the angle-identification means is adapted to correct for nonuniformity of rotation speed of the transducer means by one of scan-converting to adjust the position of data lines, change the firing rate of the transducer, and to change the speed of rotation of the rotatable means, to compensate for distortion to display in an imaging display.

11. A method for imaging body tissues from interior of a cavity in a patient's body, comprising:

(a) inserting a probe into the cavity in a patient's body, the probe having a distal end for extending inside the cavity, an ultrasonic transducer at said distal end, and a proximal end to extend outside the body;

(b) rotating a director associated with the ultrasonic transducer in the probe to transmit sequential ultrasonic pulses in an angular pattern from the distal end based on a target angular pattern and receiving ultrasonic energy reflected and scattered from the patient's body tissues at the distal end of the probe, such that each transmitted ultrasonic pulse results in a received signal (RF-line) converted from said reflected and scattered ultrasonic energy, said RF-line being use fid for subsequently forming a tissue image;

(c) determining the transmitted angular pattern by analyzing the RF-lines to determining angular separation therebetween; and (d) correcting distortion of the tissue image caused by the transmitted angular pattern, as determined by analyzing the RF-lines, being different from the target angular pattern.

12. The method of claim 11 wherein analyzing RF-lines comprises determining the similarity between RF-lines to determine the transmitted angular separation between RF-lines, wherein a high degree of similarity indicates a small angular separation and a lesser degree of similarity indicates a greater separation, the angular separation between the RF-lines determining the transmitted angular pattern.

13. The method of claim 12 wherein analyzing RF-lines comprises comparing one data line to other data lines to determine the transmitted angular pattern, the data lines being derived from the RF-lines.

14. The method of claim 13 wherein analyzing RF-lines comprises comparing data lines derived from the RF-lines, said data lines being selected from RF-lines, RF amplitude lines, RF phase lines, baseband lines, baseband amplitude lines, baseband phase lines, quantized RF phases, and quantized baseband phases, to determine the transmitted angular pattern.

15. The method of claim 13 wherein analyzing RF-lines comprises comparing data lines by calculating the cross-product among data lines as $$C_{p,p+1} = \frac{\sqrt{\sum_{m=1}^{n} |s_p(m) \cdot s_{p+1}*(m)|}}{\sqrt{\sum_{m=1}^{n} |s_p(m) \cdot s_p*(m)|}} \quad \text{Eq. 1}$$

where * denotes complex conjugation, s is the magnitude of a sample in the data line, p represents the specific data line of interest, n is the number of samples in a data line, and m is an arbitrary integer variable for summation.

16. The method of claim 13 wherein analyzing the RF-lines comprises analyzing differences between data lines.

17. The method of claim 16 wherein analyzing the RF-lines comprises analyzing root means square difference between data lines.

18. The method of claim 13 wherein analyzing RF-lines comprises analyzing the data lines to define speckle cells each having generally uniform ultrasonic energy characteristic therein and analyzing consistency of the dimensions of the speckle cells between said data lines.

19. The method of claim 13 further comprising correcting for difference between the transmitted angular pattern and the target angular pattern by adjusting the position of data lines to correct for distortions for display in an imaging display.

20. The method of claim 13 further comprising correcting for nonuniformity in the angular pattern by adjusting the transmission rate of the ultrasonic pulses to correct for distortions for display in an imaging display.

21. The method of claim 13 wherein the step of correcting distortion comprises one of scan-converting to adjust the position of data lines, change the firing rate of the transducer, and to change the speed of rotation of the rotatable means, to compensate for distortion of the tissue image in an imaging display caused by a difference between the transmitted angular pattern and the transmitted angular pattern.

22. A method for imaging body tissues from interior of a cavity in a patient's body, comprising:

(a) inserting a probe into the cavity in a patient's body, the probe having a distal end for entering the body, a proximal end to extend outside the body, and a transducer at said distal end;

(b) rotating the transducer to transmit sequential ultrasonic pulses in an angular pattern from the distal end based on a target angular pattern and receiving ultrasonic pulses reflected and scattered from the patient's body tissues at the distal end of the probe, such that each transmitted ultrasonic pulse results in a received signal (RF-line) converted from said reflected and scattered ultrasonic energy, said RF-line being useful for subsequently forming a tissue image;

(c) determining the transmitted angular pattern by analyzing data lines to determine the similarity between RF-lines to determine the angular separation between RF-lines, wherein a high degree of similarity indicates a small angular separation and a lesser degree of similarity indicates a greater separation, the angular separation between the RF-lines determining the transmitted angular pattern, the data lines being derived from the RF-lines and being selected from the group consisting of RF-lines, RF amplitude lines, RF phase lines, baseband lines, baseband amplitude lines, baseband phase lines, quantized RF phases, and quantized baseband phases; and (d) correcting distortion of the tissue image caused by the transmitted angular pattern being different from the target angular pattern, based on the transmitted angular pattern as determined by analyzing the RF-lines caused by reflection and scattering from the body tissues alone.

* * * * *